United States Patent
Hou et al.

(10) Patent No.: US 10,279,182 B2
(45) Date of Patent: May 7, 2019

(54) SYSTEM AND METHOD FOR DETERMINING A STIMULATION THRESHOLD FOR CLOSED LOOP SPINAL CORD STIMULATION

(71) Applicant: PACESETTER, INC., Sylmar, CA (US)

(72) Inventors: Wenbo Hou, Santa Clarita, CA (US); Fujian Qu, San Jose, CA (US); Stuart Rosenberg, Castaic, CA (US); Kyungmoo Ryu, Palmdale, CA (US)

(73) Assignee: PACESETTER, INC., Sylmar, CA (US)

( * ) Notice: Subject to any disclaimer, the term of this patent is extended or adjusted under 35 U.S.C. 154(b) by 170 days.

(21) Appl. No.: 15/345,163

(22) Filed: Nov. 7, 2016

(65) Prior Publication Data

US 2018/0126169 A1 May 10, 2018

(51) Int. Cl.
- *A61N 1/36* (2006.01)
- *A61N 1/05* (2006.01)
- *A61N 1/372* (2006.01)

(52) U.S. Cl.
CPC ....... *A61N 1/36139* (2013.01); *A61N 1/0551* (2013.01); *A61N 1/36071* (2013.01); *A61N 1/37247* (2013.01); *A61N 1/37264* (2013.01)

(58) Field of Classification Search
CPC ............ A61N 1/36062; A61N 1/36128; A61N 1/36135; A61N 1/36139
See application file for complete search history.

(56) References Cited

U.S. PATENT DOCUMENTS

| | | | |
|---|---|---|---|
| 7,742,823 B2 | 6/2010 | King et al. | |
| 2011/0313484 A1 | 12/2011 | Ordonez et al. | |
| 2014/0243926 A1* | 8/2014 | Carcieri | A61N 1/36071 607/46 |
| 2017/0173332 A1* | 6/2017 | Overstreet | A61N 1/0541 |
| 2017/0361101 A1* | 12/2017 | Single | A61N 1/36139 |

FOREIGN PATENT DOCUMENTS

WO 2012155188 A1 11/2012

* cited by examiner

*Primary Examiner* — Allen Porter

(57) ABSTRACT

System and methods are provided for determining a stimulation threshold for closed loop spinal cord stimulation (SCS). The system and methods provide a lead coupled to an implantable pulse generator (IPG). The system and methods deliver SCS pulses from the IPG to the lead electrodes in accordance with an SCS therapy, and determine an evoked compound action potential (ECAP) amplitude based on an ECAP waveform resulting from the SCS therapy. The system and methods increase the SCS therapy by increasing at least one of an amplitude, a duration, and number of the SCS pulses associated with the SCS therapy. The system and methods also include iteratively repeat the delivering, determining and increasing operations until the ECAP amplitude exhibits a downward trend divergence. The system and methods define a stimulation threshold based on the ECAP amplitude at the trend divergence.

14 Claims, 12 Drawing Sheets

SYSTEM AND METHOD FOR DETERMINING A STIMULATION THRESHOLD FOR CLOSED LOOP SPINAL CORD STIMULATION

FIELD OF THE INVENTION

Embodiments of the present disclosure generally relate to neurostimulation (NS) systems generating electric pulses proximate to nervous tissue, and more particularly to spinal cord stimulation (SCS) systems.

BACKGROUND OF THE INVENTION

NS systems are devices that generate electrical pulses and deliver the pulses to nervous tissue to treat a variety of disorders. For example, SCS has been used to treat chronic and intractable pain. Another example is deep brain stimulation, which has been used to treat movement disorders such as Parkinson's disease and affective disorders such as depression. While a precise understanding of the interaction between the applied electrical energy and the nervous tissue is not fully appreciated, it is known that application of electrical pulses depolarize neurons and generate propagating action potentials into certain regions or areas of nerve tissue. The propagating action potentials effectively mask certain types of pain transmitted from regions, increase the production of neurotransmitters, or the like. For example, applying electrical energy to the spinal cord associated with regions of the body afflicted with chronic pain can induce "paresthesia" (a subjective sensation of numbness or tingling) in the afflicted bodily regions. Inducing this artificial sensation replaces the feeling of pain in the body areas effectively masking the transmission of non-acute pain sensations to the brain.

Aβ sensory fibers mediate sensations of touch, vibration, and pressure from the skin. Aβ sensory fibers have been shown to be recruited at therapeutic stimulation levels and the amplitude of the Aβ potential correlates with the degree of coverage of the painful area or region. Further, the amplitude of the Aβ potential has been shown to increase with increasing stimulation current from the SCS. At high currents, additional late responses have been observed.

A concern of SCS system designs are neural damage caused by the generated electrical pulses emitted from lead electrodes of the SCS system. Conventional SCS systems are configured such that the lead electrodes are charge-balanced after the electrical pulses are emitted. However, an electrode may be polarized during deliver of the pulse that irreversible tissue damage or electrode damage can occur. Therefore, a need remains to determine a limit for the current and charge densities of the generated electrical pulses that allow charge injection be compensated by reversible processes.

SUMMARY

In accordance with one embodiment, a method for determining a stimulation threshold for closed loop spinal cord stimulation is disclosed. The method includes providing a lead coupled to an implantable pulse generator (IPG). The lead includes at least one lead electrode and is configured to be implanted at a target position proximate to nerve tissue of interest. The method also includes delivering SCS pulses from the IPG to the lead electrodes in accordance with an SCS therapy, and determining an evoked compound action potential (ECAP) amplitude based on an ECAP amplitude waveform resulting from the SCS therapy. The method further includes increasing the SCS therapy by increasing at least one of a pulse amplitude, a pulse duration, pulse frequency, burst frequency, or frequency of SCS pulse associated with the SCS therapy. The method also include iteratively repeating the delivering, determining and increasing operations until an increasing trend in the ECAP amplitude exhibits a trend divergence. The method includes defining a stimulation threshold based on the ECAP amplitude at the trend divergence.

Optionally, during the iterative operation of the method, the trend divergence is exhibited when the ECAP amplitude during an Nth iteration of the delivering, determining and increasing operation is lower than an anticipated ECAP amplitude extrapolated based on ECAP trending during the previous iterations of the delivering, determining and increasing operations.

In an embodiment, a method for determining a stimulation threshold for closed loop spinal cord stimulation (SCS) is disclosed. The method includes providing a lead coupled to an implantable pulse generator (IPG). The lead includes at least one lead electrode and is configured to be implanted at a target position proximate to nerve tissue of interest. The method also includes programming the IPG to deliver a series of SCS pulses to form a plurality of SCS waveforms from the lead electrodes. Each SCS waveform has a different stimulation amplitude. The method includes measuring evoked compound action potential (ECAP) waveforms resulting from the plurality of stimulation waveforms. Further, the method includes defining a stimulation threshold based on at least one of an amplitude, a maximum, a minimum, a slope (ascending or descending), and time delay between onset of SCS and above fiducial points of the ECAP waveforms.

In an embodiment, a system comprising a lead having at least one pair of lead electrodes, one is cathode, the other is anode. The lead is configured to be implanted at a target position proximate to or within nerve tissue of interest. The system includes an implantable pulse generator (IPG) coupled to the lead. The IPG is configured to deliver a series of SCS pulses to the lead electrodes at a predetermined amplitude. The system also includes a sensing circuitry configured to measure an evoked compound action potential (ECAP) waveform resulting from the SCS therapy, and a processor programed to operation, in response to instructions stored on a non-transient computer-readable medium. The processor, in response to the instructions, determines an ECAP amplitude based on the ECAP waveform and increases the SCS therapy by increasing at least one of a pulse amplitude, a pulse duration, a pulse frequency, burst frequency and a frequency of SCS pulses associated with the SCS therapy. The processor, in response to the instructions, also iteratively repeats the determine and increase operations until an increasing trend in the ECAP amplitude exhibits a trend divergence, and define a stimulation threshold based on the ECAP amplitude at the trend divergence.

DETAILED DESCRIPTION

Embodiments herein may be implemented with, and/or utilize aspects of, the methods and system described in the following co-pending application: U.S. patent application, titled "SYSTEM AND METHOD FOR CLOSED LOOP SPINAL CORD STIMULATION USING EVOKED COMPOUND ACTION POTENTIALS" having docket numbers A13E1047 and A13E1078, which is filed on or about the same day as the present application and is expressly incorporated herein by reference in its entirety.

Embodiments described herein include closed-loop neurostimulation (NS) systems, and methods for determining or monitoring the maximal current density based on closed loop spinal cord stimulation (SCS) systems. The NS system uses sensed neurological signals, such as an evoked compound activation potential (ECAP) from an Aβ sensory fiber or spinal cord. The closed-loop NS system may include an implantable pulse generator (IPG), which includes an algorithm that defines stimulation levels for SCS. The closed-loop NS system may further include stimulating and sensing functions of targeted nerves or spinal cord. The NS system may automatically analyze neuronal recording to estimate whether the delivered SCS is tolerable by neuronal cells. The NS system may automatically adjust SCS when ECAP recordings suggest irreversible neuronal tissue damage. The adjustment may include turning off SCS, reduce SCS amplitude, switch SCS to another configuration, or the like.

Additionally, at least one embodiment described herein automatically measures the ECAP at fixed stimulation strength on a daily or weekly basis, and transmits the ECAP recordings to an external device. The longitudinal trend of ECAP in response to a spinal cord stimulation configuration may be used to assess the health state of the neuronal cells. A decrease in ECAP trend may suggest functional deterioration of the neuronal cells, thus provide guidance to adjust SCS configuration.

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as Illustrative in nature and not restrictive.

Figure 1:
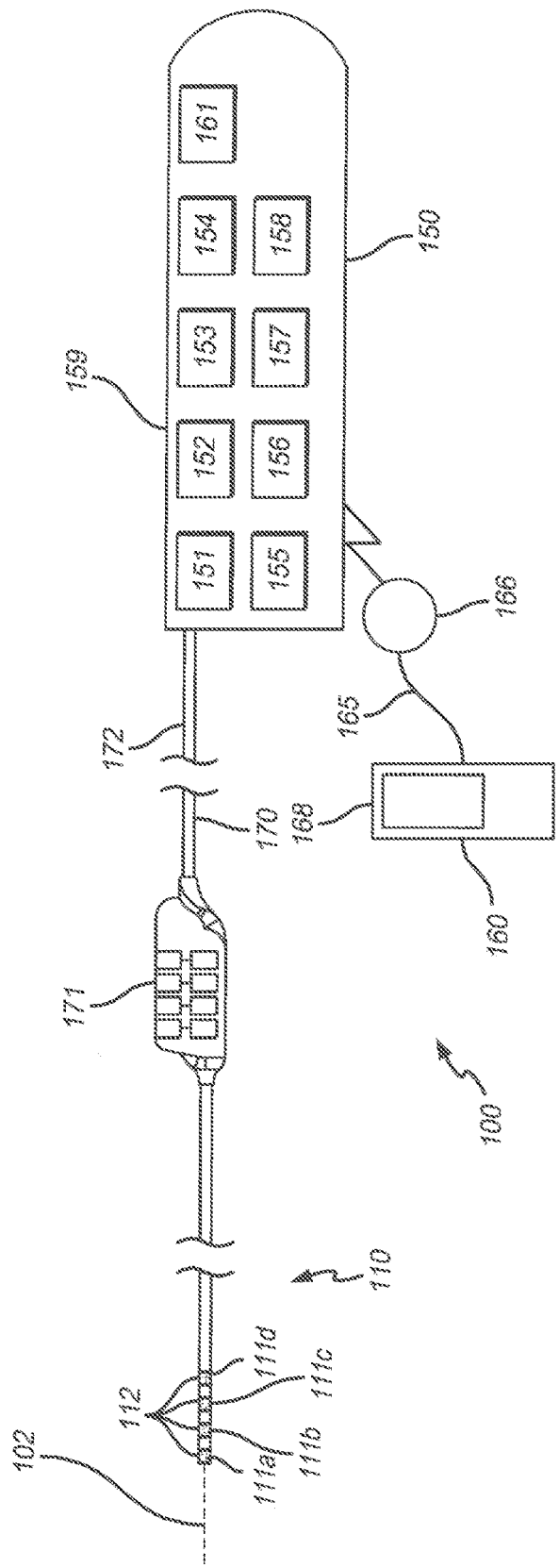
FIG. 1 illustrates a neurostimulation system, according to an embodiment of the present disclosure.

FIG. 1 depicts an NS system 100 that generates electrical pulses for application to tissue of a patient according to one embodiment. For example, the NS system 100 may be adapted to stimulate spinal cord tissue, peripheral nerve tissue, deep brain tissue, cortical tissue, cardiac tissue, digestive tissue, pelvic floor tissue, or any other suitable nerve tissue of interest within a patient's body.

The NS system 100 includes an implantable pulse generator (IPG) 150 that is adapted to generate electrical pulses for application to tissue of a patient. The IPG 150 typically comprises a metallic housing or can 159 that encloses a controller 151, pulse generating circuitry 152, a charging coil 153, a battery 154, a far-field and/or near field communication circuitry 155, battery charging circuitry 156, switching circuitry 157, sensing circuitry 158, memory 161, and the like. The controller 151 typically includes a microcontroller or other suitable processor for controlling the various other components of the device. Software code may be stored in memory 161 of the IPG 150 or integrated with the controller 151 for execution by the microcontroller or processor to control the various components of the device.

The IPG 150 may comprise a separate or an attached extension component 170. If the extension component 170 is a separate component, the extension component 170 may connect with a "header" portion of the IPG 150 as is known in the art. If the extension component 170 is integrated with the IPG 150, internal electrical connections may be made through respective conductive components. Within the IPG 150, electrical pulses are generated by the pulse generating circuitry 152 and are provided to the switching circuitry 157. The switching circuitry 157 connects to outputs of the IPG 150. Electrical connectors (e.g., "Bal-Seal" connectors) within the connector portion 171 of the extension component 170 or within the IPG header may be employed to conduct various stimulation pulses. The terminals of one or more leads 110 are inserted within connector portion 171 or within the IPG header for electrical connection with respective connectors. Thereby, the pulses originating from the IPG 150 are provided to the leads 110. The pulses are then conducted through the conductors of the lead 110 and applied to tissue of a patient via lead electrodes 111a-d. Any suitable known or later developed design may be employed for connector portion 171.

The lead electrodes 111a-d may be positioned along a horizontal axis 102 of the lead 110, and are angularly positioned about the horizontal axis 102 so the lead electrodes 111a-d do not overlap. The lead electrodes 111a-d may be in the shape of a ring such that each lead electrode 111a-d continuously covers the circumference of the exterior surface of the lead 110. Each of the lead electrodes 111a-d are separated by non-conducting rings 112, which electrically isolate each lead electrode 111a-d from an adjacent lead electrode 111a-d. The non-conducting rings 112 may include one or more insulative materials and/or biocompatible materials to allow the lead 110 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The lead electrodes 111a-d may be configured to emit the pulses in an outward radial direction proximate to or within a stimulation target. The electrodes 111a-d may also be configured to acquire electrical potential measurements (e.g., voltage, current) for the sensory circuit 158, such as evoked compound activation potentials (ECAP) emitted from the stimulation target.

Optionally, the IPG 150 may have more than one lead 110 connected via the connector portion 171 of the extension component 170 or within the IPG header. Additionally or alternatively, the electrodes 111a-d of each lead 110 may be configured separately to emit current pulses or measure the ECAP emitted from the stimulation target.

Additionally or alternatively, the lead electrodes 111a-d may be in the shape of a split or non-continuous ring such that the pulse may be directed in an outward radial direction adjacent to the lead electrodes 111a-d. Examples of a fabrication process of the lead electrodes 111a-d is disclosed in U.S. Published Application No. 2011/0072657, entitled, "METHOD OF FABRICATING STIMULATION LEAD FOR APPLYING ELECTRICAL STIMULATION TO TISSUE OF A PATIENT," which is expressly incorporated herein by reference.

It should be noted the lead electrodes 111a-d may be in various other formations, for example, in a planar formation on a paddle structure as disclosed in U.S. Provisional Application No. 61/791,288, entitled, "PADDLE LEADS FOR NEUROSTIMULATION AND METHOD OF DELIVERYING THE SAME," which is expressly incorporated herein by reference The lead 110 may comprise a lead body 172 of insulative material about a plurality of conductors within the material that extend from a proximal end of lead 110, proximate to the IPG 150, to its distal end. The conductors electrically couple a plurality of the lead electrodes 111a-d to a plurality of terminals (not shown) of the lead 110. The terminals are adapted to receive electrical pulses and the lead electrodes 111a-d are adapted to apply the pulses to the stimulation target of the patient. Also, sensing of physiological signals may occur through the lead electrodes 111a-d, the conductors, and the terminals. It should be noted that although the lead 110 is depicted with four lead electrodes 111a-d, the lead 110 may include any suitable number of lead electrodes 111a-d (e.g., less than four, more than four) as well as terminals, and internal conductors. Additionally or alternatively, various sensors (e.g., a position detector, a radiopaque fiducial) may be located near the distal end of the lead 110 and electrically coupled to terminals through conductors within the lead body 172.

Although not required for all embodiments, the lead body 172 of the lead 110 may be fabricated to flex and elongate upon implantation or advancing within the tissue (e.g., nervous tissue) of the patient towards the stimulation target and movements of the patient during or after implantation. By fabricating the lead body 172, according to some embodiments, the lead body 172 or a portion thereof is capable of elastic elongation under relatively low stretching forces. Also, after removal of the stretching force, the lead body 172 may be capable of resuming its original length and profile. For example, the lead body may stretch 10%, 20%, 25%, 35%, or even up or above to 50% at forces of about 0.5, 1.0, and/or 2.0 pounds of stretching force. Fabrication techniques and material characteristics for "body compliant" leads are disclosed in greater detail in U.S. Provisional Patent Application No. 60/788,518, entitled "Lead Body Manufacturing," which is expressly incorporated herein by reference.

For implementation of the components within the IPG 150, a processor and associated charge control circuitry for an IPG is described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 156) of an IPG using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference.

An example and discussion of "constant current" pulse generating circuitry (e.g., pulse generating circuitry 152) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IPG 150. Different pulses on different lead electrodes 111a-d may be generated using a single set of the pulse generating circuitry 152 using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of such circuitry may be employed to provide pulse patterns (e.g., tonic stimulation waveform, burst stimulation waveform) that include generated and delivered stimulation pulses through various lead electrodes of one or more leads 111a-d as is also known in the art. Various sets of parameters may define the pulse characteristics and pulse timing for the pulses applied to the various lead electrodes 111a-d as is known in the art. Although constant current pulse generating circuitry is contemplated for some embodiments, any other suitable type of pulse generating circuitry may be employed such as constant voltage pulse generating circuitry.

The sensing circuitry 158 may measure an electric potential (e.g., voltage, current) over time of the stimulation target or tissue through at least one of the electrodes 111a-d proximate to the stimulation target configured to measure the electrical potential. For example, the sensing circuitry 158 may measure an evoked compound activation potential (ECAP) waveform from an Aβ sensory fiber or spinal cord. Optionally, the sensing circuitry 158 may store the electric potential on the memory 161.

An external device 160 may be implemented to charge/recharge the battery 154 of the IPG 150 (although a separate recharging device could alternatively be employed), to access the memory 161, and to program the IPG 150 on the pulse specifications while implanted within the patient. Although, in alternative embodiments separate programmer devices may be employed for charging and/or programming the NS system 100. The external device 160 may be a processor-based system that possesses wireless communication capabilities. Software may be stored within a non-transitory memory of the external device 160, which may be executed by the processor to control the various operations of the external device 160. A "wand" 165 may be electrically connected to the external device 160 through suitable electrical connectors (not shown). The electrical connectors may be electrically connected to a telemetry component 166 (e.g., inductor coil, RF transceiver) at the distal end of wand 165 through respective wires (not shown) allowing bi-directional communication with the IPG 150. Optionally, in some embodiments, the wand 165 may comprise one or more temperature sensors for use during charging operations.

The user may initiate communication with the IPG 150 by placing the wand 165 proximate to the NS system 100. Preferably, the placement of the wand 165 allows the telemetry system of the wand 165 to be aligned with the far-field and/or near field communication circuitry 155 of the IPG 150. The external device 160 preferably provides one or more user interfaces 168 (e.g., touchscreen, keyboard, mouse, buttons, or the like) allowing the user to operate the IPG 150. The external device 160 may be controlled by the user (e.g., doctor, clinician) through the user interface 168 allowing the user to interact with the IPG 150. The user interface 168 may permit the user to move electrical stimulation along and/or across one or more of the lead(s) 110 using different lead electrode 111a-d combinations, for example, as described in U.S. Published Application No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference. Optionally, the user interface 168 may permit the user to designate which electrodes 111a-d are to stimulate (e.g., emit current pulses, in an anode state, in a cathode state) the stimulation target, to measure the ECAP (e.g., connecting to the sensing circuitry 158) resulting from the current pulses, remain inactive (e.g., floating), or the like. Additionally or alternatively, the external device 160 may access or download the electrical measurements from the memory 161 acquired by the sensing circuitry 158.

Also, the external device 160 may permit operation of the IPG 150 according to one or more spinal cord stimulation (SCS) programs or therapy to treat the patient. Each SCS program may include one or more sets of stimulation parameters of the pulse including pulse amplitude, stimulation level, pulse width, pulse frequency or inter-pulse period, pulse repetition parameter (e.g., number of times for a given pulse to be repeated for respective stimset during execution of program), biphasic pulses, monophasic pulses, etc. The IPG 150 modifies its internal parameters in response to the control signals from the external device 160 to vary the stimulation characteristics of the stimulation pulses transmitted through the lead 110 to the tissue of the patient. NS systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are expressly incorporated herein by reference.

Figure 2:
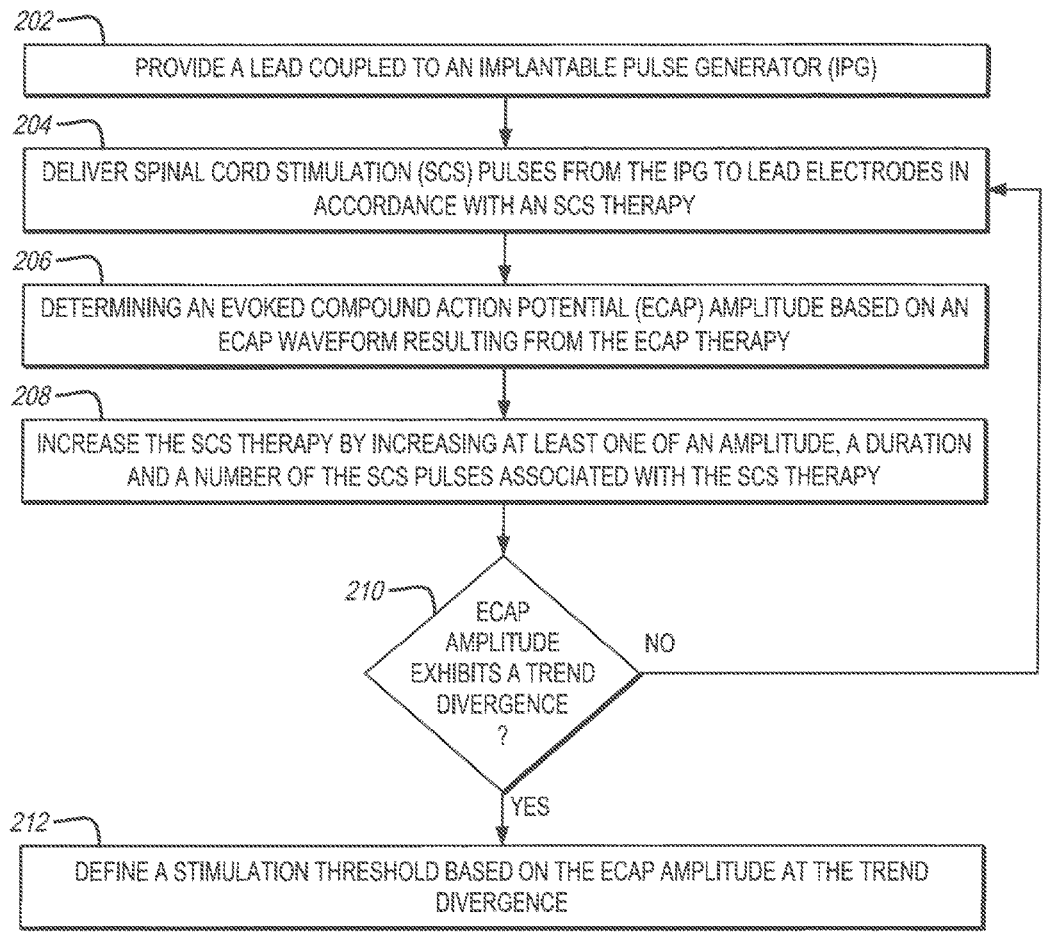
FIG. 2 is a flowchart of a method for closed loop spinal cord stimulation, according to an embodiment of the present disclosure.
Figure 9:
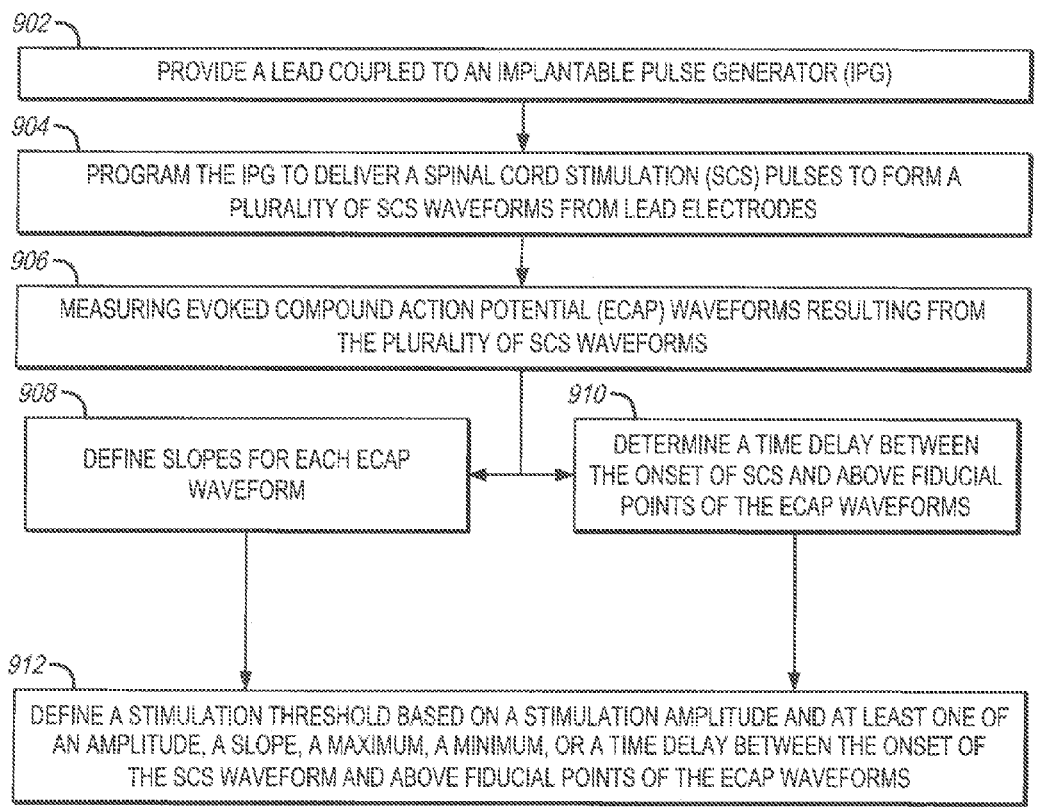
FIG. 9 is a flowchart of a method for closed loop spinal cord stimulation, according to an embodiment of the present disclosure.

FIGS. 2 and 9 are flowcharts of a method 200 and 900, respectively, for determining a stimulation threshold for closed loop spinal cord stimulation. The methods 200 and 900, for example, may employ structures or aspects of various embodiments (e.g., systems and/or methods) discussed herein. For example, an implantable pulse generator (IPG) may be similar to the IPG 150 (FIG. 1) or may include other features, such as those described or referenced herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. Furthermore, it is noted that the following is just one possible method of performing simultaneous burst and tonic stimulation. It should be noted, other methods may be used, in accordance with embodiments herein.

One or more methods may (i) provide a lead coupled to an implantable pulse generator (IPG), (ii) deliver spinal cord stimulation (SCS) pulses from the IPG to the lead electrodes in accordance with an SCS therapy, (iii) determine an evoked compound action potential (ECAP) amplitude based on an ECAP waveform resulting from the SCS therapy, (iv) increase the SCS therapy by increasing at least one of an amplitude, a duration and a number of the SCS pulses associated with the SCS therapy, (v) iteratively repeat the delivering, determining and increasing operations until the ECAP amplitude exhibits a trend divergence, and (vi) defining a stimulation threshold based on the ECAP amplitude at the trend divergence.

Figure 3:
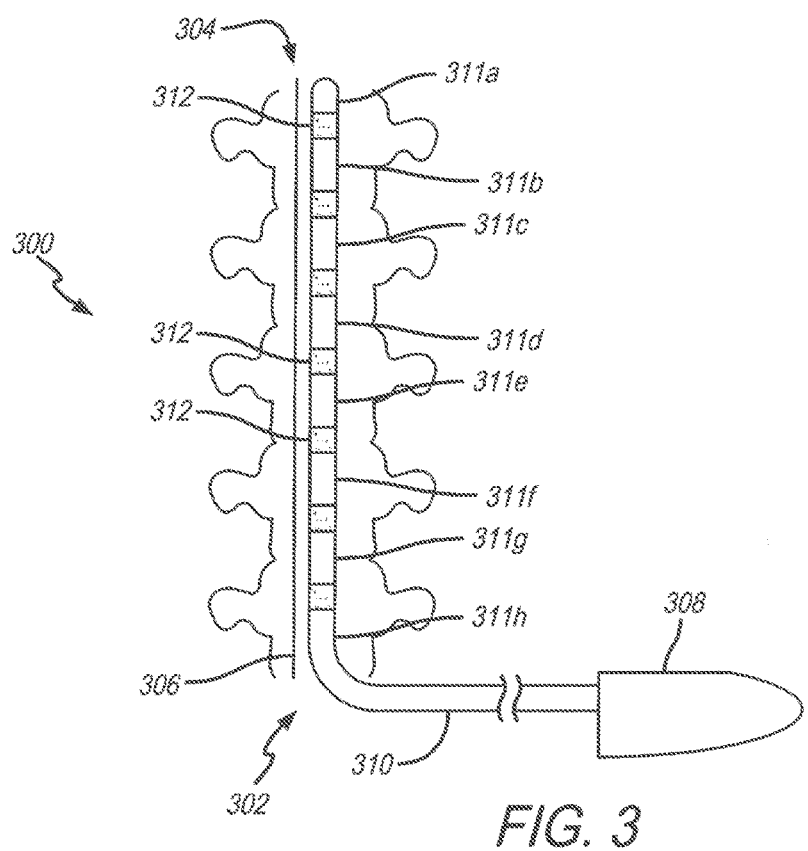
FIG. 3 illustrates a lead placement for spinal cord stimulation of a patient, according to an embodiment of the present disclosure.

Beginning at 202, the method 200 provides a lead 304 coupled to an implantable pulse generator (IPG) 308. FIG. 3 is an illustration of a lead placement 300 for SCS. The lead 304 is positioned at a target position, in an epidural space 302, of a patient so as to be in close proximity to a nerve tissue of interest, a spinal cord 306. The lead 304 includes eight electrodes 311a-h that are each separated by non-conducting rings 312. The lead 304 is connected via a lead body 310 to the IPG 308. It should be noted, that in alternative embodiments the lead 304 may have a fewer than or greater than the number of lead electrodes 311a-h shown in FIG. 3. For example, the lead 304 may have a single lead electrode 311a used in conjunction with the can (e.g., the can 159) during the SCS pulses in a cathode or anode state.

At 204, the method 200 delivers spinal cord stimulation (SCS) pulses 406 from the IPG 308 to lead electrodes 311a-h in accordance with an SCS therapy. The IPG may be programmed to deliver SCS pulses to the lead electrodes 311a-h through the lead body 310 at a predetermined amplitude. For example, the IPG 150 may be programmed or receive stimulation programs representing the SCS therapy from the external device 160. The SCS therapy may include different SCS waveforms formed by the SCS pulses 406, such as a burst stimulation waveform, a tonic stimulation waveform, a biphasic pulse, or the like, which are emitted from one or more of the lead electrodes 311a-h. The SCS therapy may include predetermined electrical characteristics of the SCS pulses 406, such as, amplitude 410, 412, duration (e.g., pulse width) 414, 416, and number of the SCS pulses for each SCS waveform.

Figure 4:
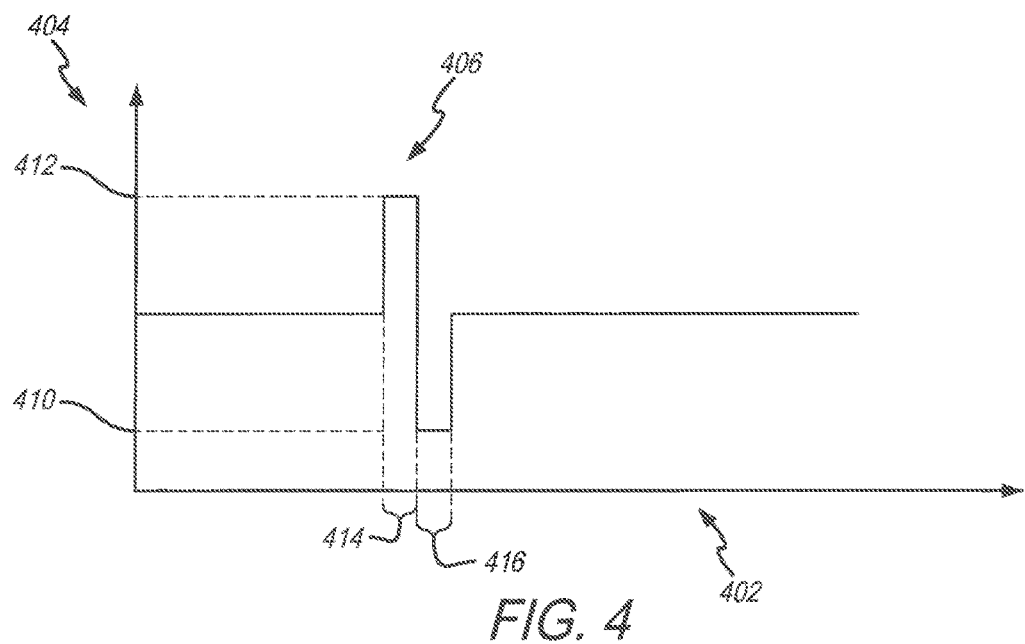
FIG. 4 is a graphical representation of a spinal cord stimulation pulse delivered to a lead electrode based on a spinal cord stimulation therapy, according to an embodiment of the present disclosure.

FIG. 4 illustrates a series of SCS pulses 406 delivered by the IPG 308 and emitted by one or more of the lead electrodes 3111a-h at a predetermined amplitude (e.g., a positive amplitude 412, a negative amplitude 410) and duration 414, 416 in accordance with an embodiment. A horizontal axis 402 represents time, and a vertical axis 404 may represent voltage or electrical potential. For example, the SCS pulses 406 may be emitted from the lead electrode 311e, which is configured in a cathode state (e.g., electrically coupled to the common ground), and the lead electrodes 311d and 311f, which are configured in an anode state (e.g., electrically coupled to the battery 154). It should be noted that the SCS pulses 406 may be generated by more lead electrodes 311a-h, fewer lead electrodes 311a-h, and/or other combinations of lead electrodes 311a-h of the lead 304. The series of SCS pulses 406 form a SCS waveform, such as a tonic or biphasic stimulation waveform. It should be noted that in other embodiments the SCS pulses 406 may form other SCS waveforms (e.g., burst stimulation waveform). It should be noted that although the amplitudes 410 and 412 are shown being equal in magnitude, alternative embodiments may not. For example, the positive amplitude 412 may have a greater amplitude than the negative amplitude 410. It should be noted that although the durations 414 and 416 of the SCS pulses 406 are shown being equal in length (e.g., pulse width), alternative embodiments may not. For example, the duration 414 of the SCS pulse 406 corresponding to the positive amplitude 412 may be longer or shorter in length (e.g., pulse width) than the duration 416 of the SCS pulse 406 corresponding to the negative amplitude 410.

Figure 5:
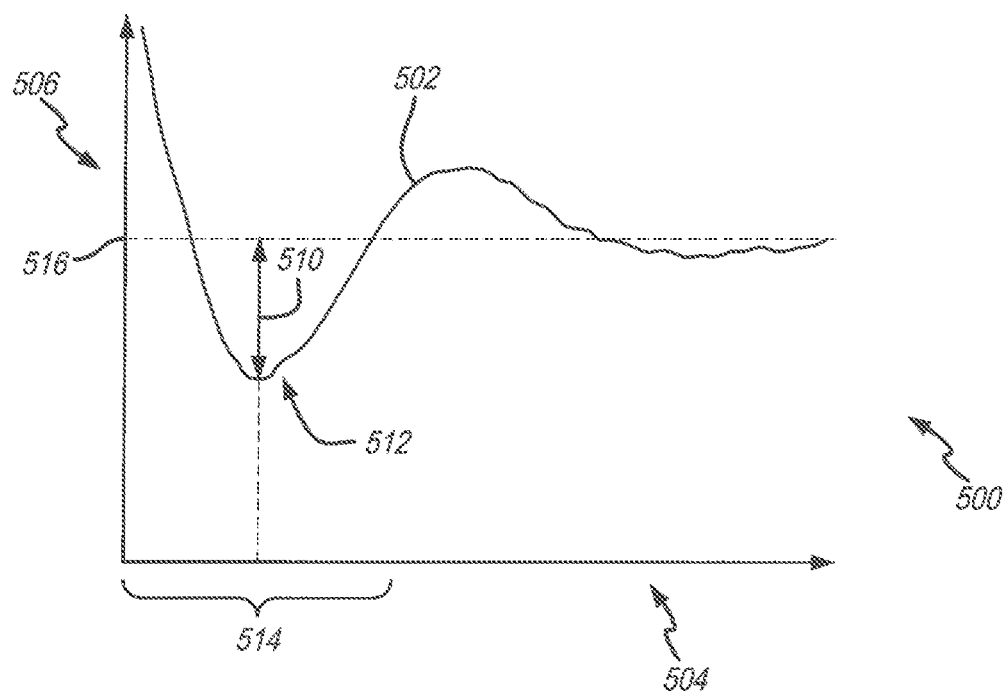
FIG. 5 is a graphical representation of a sensed evoked compound action potential at a sensing electrode proximate to a lead electrode, according to an embodiment of the present disclosure

At 206, the method 200 determines an ECAP amplitude 510 based on an ECAP waveform 502 resulting from the ECAP therapy. FIG. 5 is a graphical representation 500 of an ECAP waveform 502 measured proximate to the nerve tissue of interest (e.g., the spinal cord 308, Aβ sensory fibers). A horizontal axis 504 represents time, and a vertical axis 506 may represent voltage or electrical potential. The sensing circuitry 158 may acquire the ECAP waveform 502, resulting from the SCS pulses 406, by measuring a voltage or electrical potential of one or more of the lead electrodes 311a-h proximate to the nerve tissue of interest. The sensing circuitry 158 may utilize one or more of the lead electrodes 311a-h to measure the ECAP waveform 502. Optionally, the sensing circuitry 158 may measure the ECAP waveform 502 utilizing one or more combinations of electrodes 311a-h. In at least one embodiment, the ECAP waveform 502 may be stored by the controller 151 or sensing circuitry 158 to the memory 161, for example, onto a stimulation database with the corresponding electrical specifications (e.g., amplitude, frequency, waveform configuration, duration, number of SCS pulses 406) of the SCS pulses 406. Additionally or alternatively, the ECAP waveforms may be transmitted by the communication circuitry 155 to the external device 160.

The ECAP amplitude 510 may be determined by the controller 151 based on a peak 512 during a predetermined time period 514 of the ECAP waveform 502 with respect to a baseline 516 (e.g., common ground of the NS system 100). The ECAP amplitude 510 may be stored by the controller 151 to the memory 161, for example, onto the stimulation database. Optionally, the ECAP amplitude 510 may be transmitted to the external device 160 by the communication circuitry 155. The predetermine time period 514 may be based on when the SCS pulse is emitted from the electrodes 311a-h. For example, the predetermined time period 514 may be based on a set amount of time, such as 1.3 ms, after the SCS pulses 406. It should be noted that in other embodiments the set amount of time may be less than or greater than 1.3 ms.

Figure 6A:
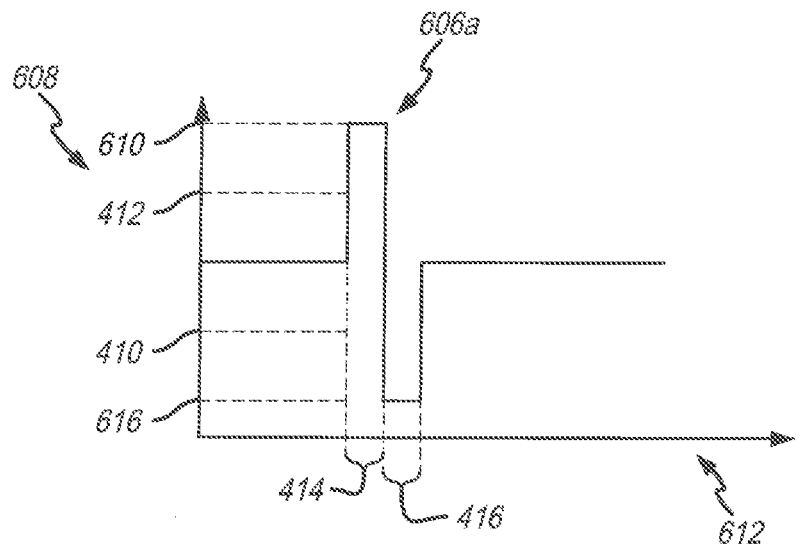
FIG. 6A is a graphical representation of a spinal cord stimulation pulse with increased amplitude in comparison to the spinal cord stimulation pulse in FIG. 4.
Figure 6B:
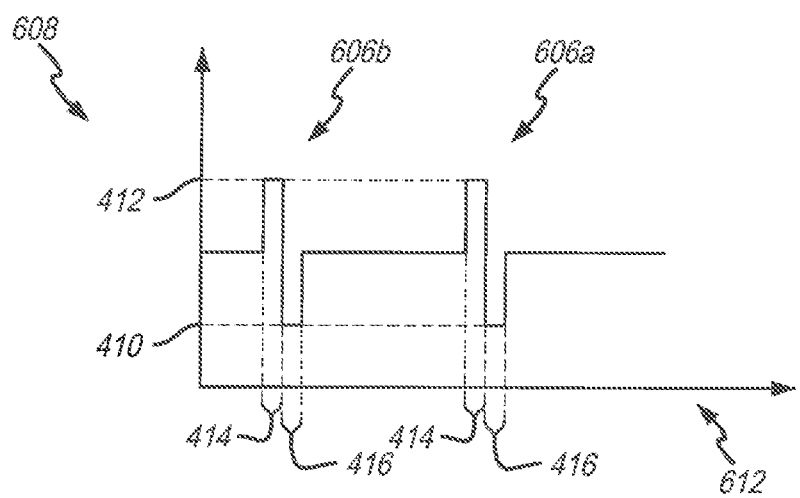
FIG. 6B is a graphical representation of a spinal cord stimulation with increased frequency of SCS pulses in comparison to the spinal cord stimulation pulse in FIG. 4.
Figure 6C:
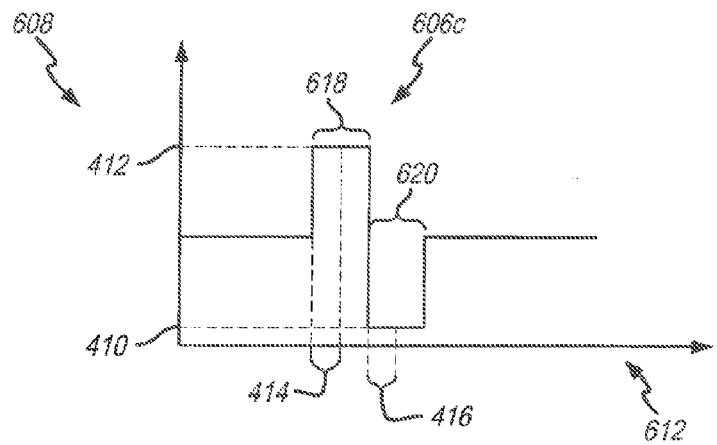
FIG. 6C is a graphical representation of a spinal stimulation pulse with increased pulse width in comparison to the spinal cord stimulation pulse in FIG. 4.

At 208, the method 200 increases the SCS therapy by increasing at least one of the amplitude 414, 416, the duration 414, 416, and the number of SCS pulses 406 associated with the SCS therapy. For example, the controller 151 may increase at least one of the characteristics (e.g., the amplitude 414, 416, the duration 414, 416, and the number of SCS pulses 406) of the SCS pulses 406 delivered by the IPG 308. FIGS. 6A-C are graphical representations of SCS pulses 606a-c with increased SCS therapies relative to the SCS pulses 406 from FIG. 4. A horizontal axis 612 represents time, and a vertical axis 608 may represent voltage or electrical potential.

FIG. 6A illustrates SCS pulses 606a with an Increased amplitude 610 and 616 over the amplitudes 414 and 416 of the SCS pulses 406. It should be noted that in other embodiments the duration 414, the duration 416 and/or the number of the SCS pulses 606a may be increased as well. It should be noted that although the amplitudes 610 and 616 are shown being increased in equal magnitude, alternative embodiments may not. For example, the positive amplitude 610 may have a greater amplitude than the negative amplitude 616.

FIG. 6B illustrates SCS pulses 606b with an increased number of SCS pulses 606b relative to the SCS pulses 406. It should be noted that in other embodiments the duration 414, the duration 416, the amplitude 410 and/or the amplitude 412 of the SCS pulses 606b may be increased as well.

FIG. 6C Illustrates SCS pulses 606c with an increased duration 618 and 620 (e.g., pulse width) relative to the duration 414 and 416 of the SCS pulses 406. It should be noted that in other embodiments the amplitude 410 and 412 and/or number of the SCS pulses 606c may be increased as well. It should be noted that although the durations 618 and 620 are shown being increased in equal magnitude, alternative embodiments may not. For example, the duration 618 may be longer than the duration 620.

Figure 7:
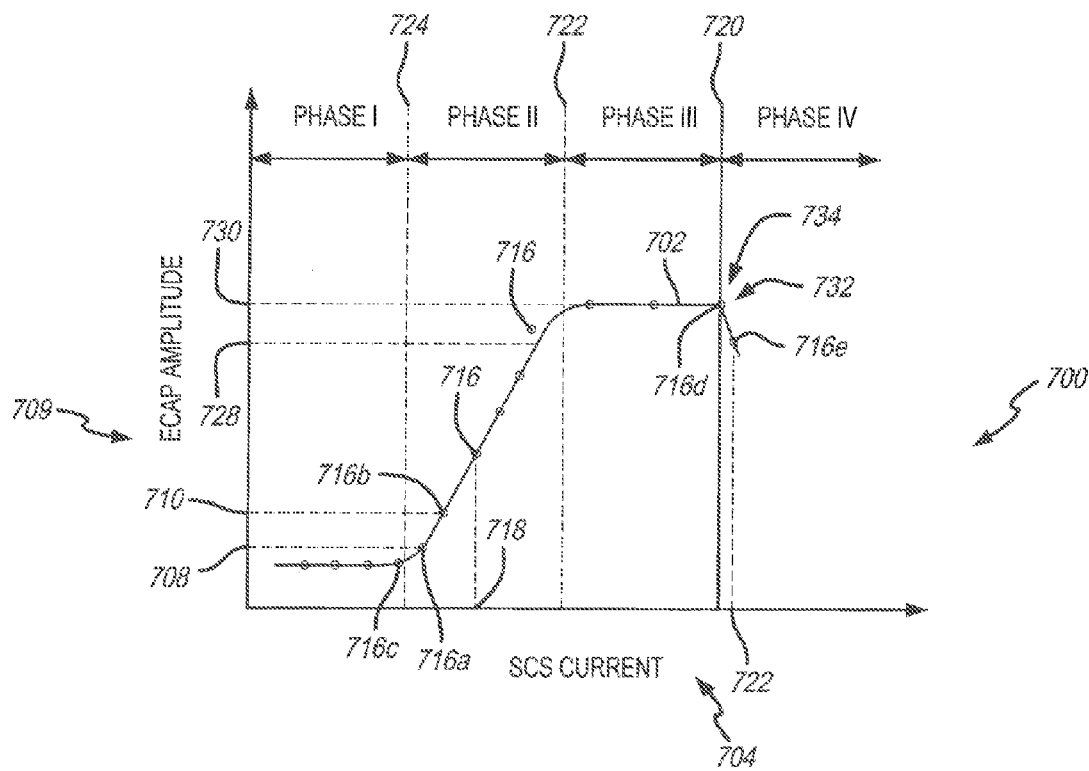
FIG. 7 is a graphical representation of the relationship between spinal cord stimulation current level and evoked compound action potential amplitudes, according to an embodiment of the present disclosure.

At 210, the method 200 determines whether the ECAP amplitude 716 exhibits a trend divergence 732. FIG. 7 is a graphical representation 700 of ECAP amplitudes 716 plotted over amplitudes (e.g., the positive amplitude 412, the negative amplitude 410, the positive amplitude 610, the negative amplitude 616) of the SCS pulses (e.g., SCS pulses 406, 606a-c) along the horizontal axis 704. It should be noted that in other embodiments, the ECAP amplitudes 716 may be plotted over the duration (e.g., the pulse width) and/or number of the SCS pulses. A vertical axis 706 represents a voltage or electrical potential magnitude of the ECAP amplitudes 716. The controller 151 may compare ECAP amplitudes 716 at a given SCS current level over ECAP amplitudes at lower SCS current levels to identify or determine whether a trend divergence 732, such as a downward trend divergence, is exhibited by the ECAP amplitudes 716.

The graphical representation 700 includes an ECAP amplitude line graph 702 illustrating the non-linear relationship between the amplitudes of the SCS pulses and the ECAP amplitudes 716, which may be characterized in phases I-IV transitioning at current amplitudes at 720, 724 and 726.

For example, in phase I the ECAP amplitudes 716 remain approximately parallel to the horizontal axis 704. In phase II, when the current amplitudes are between 724 and 726, the ECAP amplitudes 716 increase (e.g., positive slope) in a linear fashion. In phase III, when the current amplitude are between 720 and 726, the ECAP amplitudes 716 reach a plateau and are approximately parallel to the horizontal axis 704. In phase IV, when the current amplitudes are above 720 (e.g., the stimulation threshold 734), the ECAP amplitudes 716 start to decrease or enter a break down region, which indicate overstimulation and impaired neuronal functions of the nerve tissue of interest. The transition from phase III to phase IV may occur around a divergence inflection point or point of trend divergence, such as a downward trend divergence, corresponding to a sign (e.g., from positive to negative, from near zero to negative) change of the slope of the ECAP amplitude line graph 702. For example, the divergence inflection point corresponds to the onset of a negative slope of the ECAP amplitude line graph 702.

The controller 151 may identify the trend divergence by iteratively deliver (e.g., the method 200 at 204), determine (e.g., the method 200 at 206) and increase (e.g., the method 200 at 208) operations to ascertain the stimulation threshold 734 that corresponds to the start of phase IV (e.g., the divergence inflection point). For example, the controller 151 determines the ECAP amplitude 716b having a voltage at 710 from the sensor circuitry 158 measurements of the corresponding ECAP waveform. The ECAP amplitude 716b may be the result of the SCS pulses 406. The controller 151 compares the ECAP amplitude 716b with the previous ECAP amplitude, the ECAP amplitude 716a, stored on the memory 161. The ECAP amplitude 716a has a voltage at 708. The controller 151 determines, based on the voltages 708-710, that the ECAP amplitude 716b is greater than the ECAP amplitude 716a, and increases the SCS therapy by, for example, increasing the amplitude 410 and 412 of the SCS pulses 406 to attain an amplitude of the SCS pulses at 718. In at least one embodiment, the controller 151 may increase the SCS therapy at a rate or a predetermined amount. Optionally, the increase or adjustment of the SCS therapy may be received by the IPG 308 from the external device 160.

If, at 210, the ECAP amplitude 716 does not exhibit the trend divergence 732, for example, determined by the controller 151, the method 200 returns to 204 to deliver the SCS pulses (e.g., the SCS pulses 606a-c) from the IPG 308 to the same stimulation location (e.g. electrodes 311a-h) in accordance with the increased SCS therapy previously increased at 208.

The controller 151 may repeat the above process until the ECAP amplitude 716 exhibits the trend divergence 732 (e.g., decrease in ECAP amplitude 716 after an increasing trend and/or a plateau in the ECAP amplitudes indicating that the ECAP amplitude 716 is in phase IV). Optionally, the trend divergence 732 is exhibited when the ECAP amplitude 716 during an Nth iteration of the delivering (e.g., at 204 of the method 200), determining (e.g., at 206 of the method 200) and increasing (e.g., at 208 of the method 200) operations is lower than the ECAP amplitude 716 during an N−1 iteration or a plurality of previous iterations of the delivering, determining and increasing operations.

For example, the controller 151 determines, during the thirteenth iteration of the method 200, the ECAP amplitude 716e has a voltage potential at 728. The ECAP amplitude 716e is the result of SCS pulses (e.g., the SCS pulses 606a) having amplitudes at 722. The controller 151 compares the ECAP amplitude 716e with a plurality or several previous iterations, such as the tenth, eleventh, and twelfth iterations, which may be stored on the memory 161. For example, during the twelfth iteration the controller 151 determined the ECAP amplitude 716d had a voltage at 730. The controller 151 compares the voltages 728-730 of the ECAP amplitudes 716d-e. The controller 151 determines that the ECAP amplitude 716e is lower than the ECAP amplitude 716d. The controller 151 may determine that the ECAP amplitude 716e exhibits the trend divergence 732 if the ECAP amplitudes of the plurality of previous iterations are each greater than the ECAP amplitude 716e. Additionally or alternatively, the controller 151 may calculate an average ECAP amplitude from the previous iterations, which is compared with the ECAP amplitude 716e. It should be noted that the number of previous iteration may be greater than or less than three.

Optionally, the controller 151 may compare the amplitude differences between the ECAP amplitude 716d and the ECAP amplitude 716e with a threshold. For example, the controller 151 may determine that the ECAP amplitude 716e is lower than the ECAP amplitude 716d if the ECAP amplitude 716e is lower than the ECAP amplitude 716d by at least the threshold. Optionally, the threshold may be predetermined value stored on the memory 161 and/or received by the external device 160. Additionally or alternatively, the threshold may be based on the plurality of ECAP amplitudes corresponding to an average difference between two select concurrent ECAP amplitudes from the plurality of ECAP amplitudes.

If at 210, the ECAP amplitude 716 does exhibit the trend divergence 732, then at 212, the stimulation threshold 734 is defined based on the ECAP amplitude 716e at the trend divergence 732. For example, the controller 151 determines that the ECAP amplitude 716e exhibits the trend divergence 732. The ECAP amplitude 716e resulted from the SCS therapy having SCS pulses (e.g., the SCS pulses 608a) with amplitudes at 720. Based on the ECAP amplitude 716e, the controller 151 defines the stimulation threshold 734 at the SCS pulse amplitude 720 that resulted in the ECAP amplitude 716e.

The stimulation threshold 734 may be used by the controller 151 to limit the amplitude of the SCS pulses during the SCS therapy. For example, the controller 151 may have the IPG 308 deliver SCS pulses with amplitudes at or below the stimulation threshold 734. It should be noted that in other embodiments the stimulation threshold 734 may not be defined by the amplitude of the SCS pulses, for example, defined by the duration and/or number of the SCS pulses. Additionally or alternatively, the stimulation threshold 734 may be defined by combinations of electrical characteristics of the SCS pulses, for example, the stimulation threshold 734 may define the duration and amplitude of the SCS pulses, the number and amplitude of the SCS pulses, and the like.

Optionally, the method 200 may include transmitting an alert notification once the stimulation threshold 734 is defined. For example, the controller 151 may instruct the communication circuitry 155 to transmit an alert notification to the external device 160.

Optionally, the method 200 may define a suprathreshold zone and a subthreshold zone based on the stimulation threshold 734 for the SCS pulses 406. For example, once the stimulation threshold 734 is defined the controller 151 may define the suprathreshold zone by a suprathreshold predetermined value (e.g., 5 mA) above the stimulation threshold 734. The subthreshold zone may be defined by a subthreshold predetermined value (e.g., 5 mA) below the stimulation threshold 734.

Figure 8:
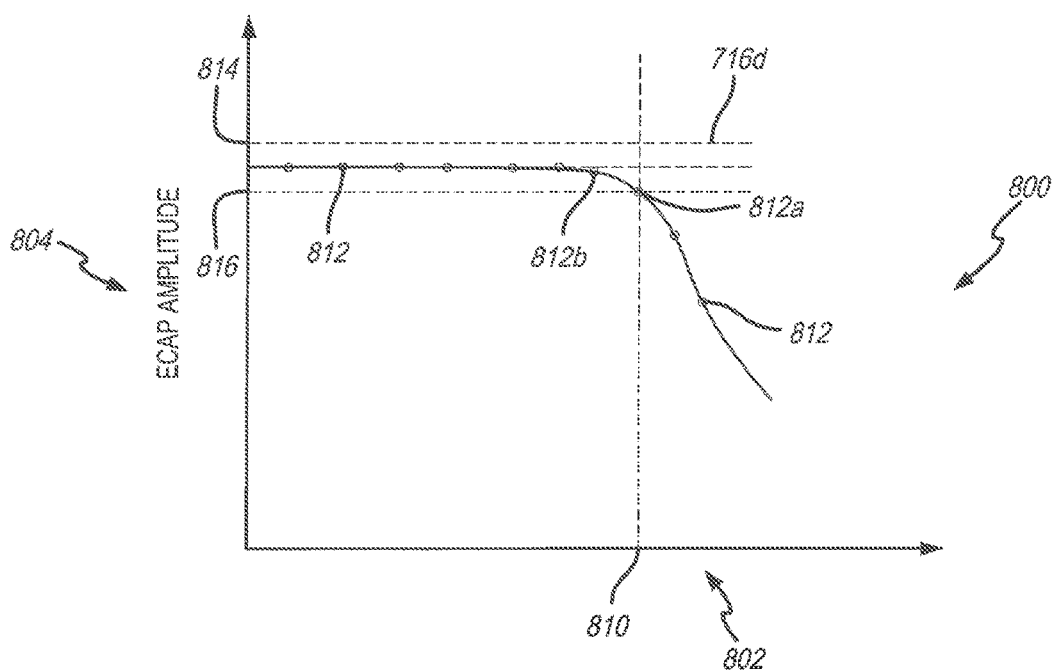
FIG. 8 is a graphical representation of evoked compound action potential amplitude changes over time in response to a similar spinal cord stimulation pulse, according to an embodiment of the present disclosure.

Optionally, the method 200 may include delivering a series of SCS pulses (e.g., the SCS pulses 406) that have an amplitude at or below the stimulation threshold 734, once the stimulation threshold 734 is defined at 212. Additionally, the method 200 may reduce the stimulation threshold 734 when an instantaneous ECAP amplitude 812a is lower than an averaged ECAP amplitude 814. FIG. 8 is a line graph 800 of ECAP amplitudes 812 plotted over time along the horizontal axis 802. A vertical axis 804 represents a voltage or electrical potential of the ECAP amplitudes 812 in response to a fixed SCS stimulation at different times, for example, the repeated SCS pulses have the same amplitude (e.g., current), frequency, or the like. The ECAP amplitudes 812 may be based on ECAP waveforms (e.g., the ECAP waveform 502) resulting from SCS pulses having an amplitude at or below the stimulation threshold 734 delivered by the IPG 308.

The averaged ECAP amplitude 814 may be based on one or more previously measured ECAP amplitudes (e.g., the ECAP amplitudes 812) measured by the IPG 308. The controller 151 may continually calculate an average ECAP amplitude based on previously measured ECAP amplitudes 812. For example, the ECAP amplitudes 812, before the time 810, have an averaged ECAP amplitude at 814.

After the time 810, the ECAP amplitudes 812 decrease. The controller 151 may identify the decrease in ECAP amplitudes 812 by comparing the instantaneous ECAP amplitude 812a and the averaged ECAP amplitude 814 based on the previous ECAP amplitude measurements. Optionally, the controller 151 may compare the difference between the ECAP amplitude 812a and the averaged ECAP amplitude 814 with a predetermined threshold 816. Once the controller 151 determines that the ECAP amplitude 812 is decreasing, the controller 151 may reduce the stimulation threshold 734. Optionally, the controller 151 may reduce the stimulation threshold 734 by a predetermined amount. Optionally, the controller 151 may change the configuration of the SCS pulses, for example, from a tonic stimulation waveform to a burst stimulation waveform. Optionally, the controller 151 may adjust the duration and/or number of the SCS pulses. Additionally or alternatively, the controller 151 may have the IPG 308 stop delivering the SCS pulses to the lead electrodes 311a-h. Optionally, the controller 151 may instruct the communication circuitry 155 to transmit an alert notification to the external device 160.

Optionally, the method 200 may include determining a stimulation baseline for the SCS pulses 406 based on a change in amplitude of the ECAP waveform 502. The stimulation baseline indicates the current amplitude at 724, which is the transition boundary between phase I and II shown in FIG. 7. The stimulation baseline indicates a minimum amplitude of the SCS pulses that will recruit neurons at the nerve tissue of interest. Recruitment of the neurons is shown as the increase in the ECAP amplitudes 816 after the current amplitude at 724. The controller 151 may determine the stimulation baseline when the ECAP amplitude 816 increases a predetermined amount during the iterative process described above, for example, when comparing the ECAP amplitude 716a with the ECAP amplitude 716c to determine whether the ECAP amplitude exhibits a trend divergence.

One or more methods may (i) provide a lead coupled to the IPG, (ii) program the IPG to deliver spinal cord stimulation (SCS) pulses to form a plurality of SCS waveforms from the lead electrodes, (iii) measure ECAP waveforms resulting from the plurality of SCS waveforms, and (iv) define a stimulation threshold based on at least one of an amplitude, a slope (ascending or descending), a maximum, a minimum, or time delay between the onset of SCS and above one or more fiducial points of the ECAP waveforms.

Beginning at 902, the method 900 provides a lead 304 coupled to an implantable pulse generator (IPG) 308.

Figure 10:
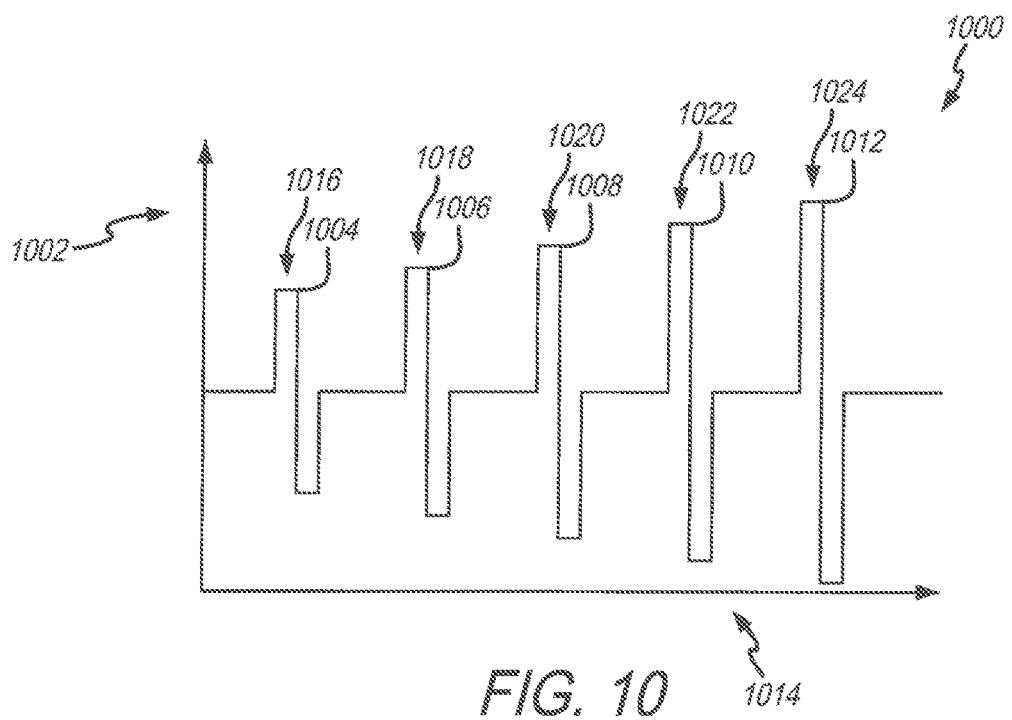
FIG. 10 is a graphical representation of spinal cord stimulation pulses forming a plurality of spinal cord stimulation waveforms delivered to a lead electrode, according to an embodiment of the present disclosure.

Next at 904, the IPG 308 is programmed to deliver SCS pulses 1000 to the lead electrodes 3111a-h to form a plurality of SCS waveforms 1016-1024 from the lead electrodes 311a-h. FIG. 10 illustrates a series of SCS pulses 1000 delivered by the IPG 308 and emitted by the lead electrodes 3111a-h at various predetermined stimulation amplitudes 1004-1012 increasing over time, in accordance with an embodiment. A horizontal axis 1014 represents time, and a vertical axis 1002 may represent voltage or electrical potential. The series of SCS pulses 1000 form SCS waveforms 1016-1024 illustrated as tonic or biphasic stimulation waveforms. However, it should be noted that in other embodiments the SCS pulses 1000 may form other SCS waveforms (e.g., burst stimulation waveform).

Figure 11:
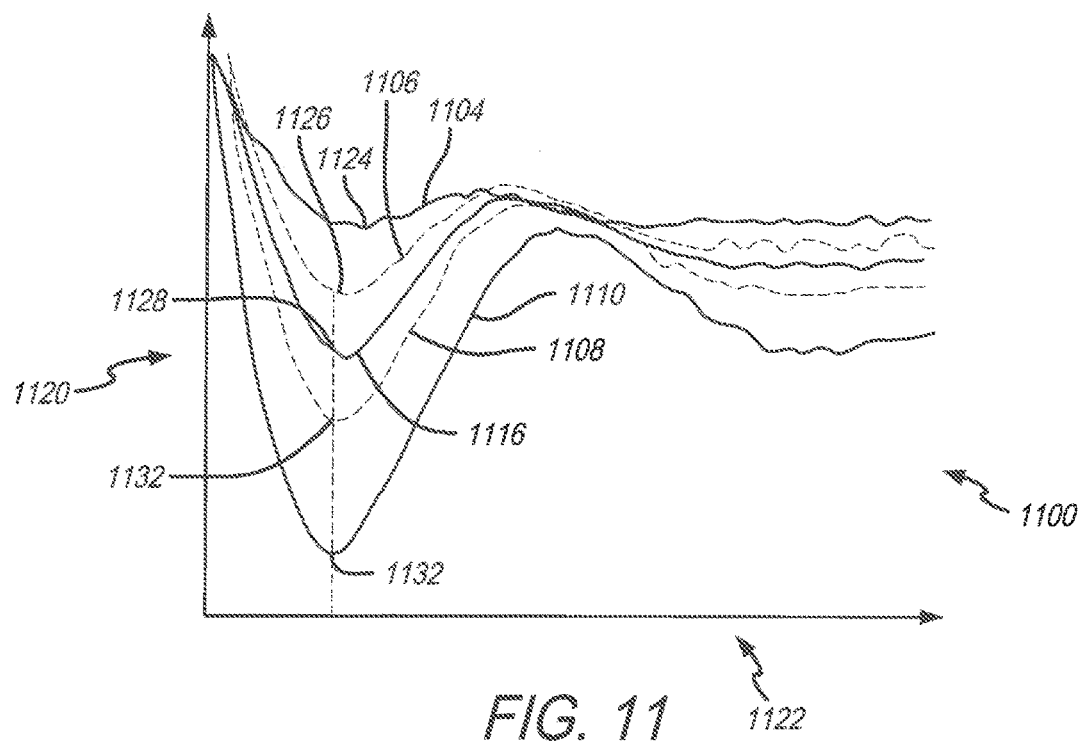
FIG. 11 is a graphical representation of evoked compound action potential waveforms, according to an embodiment of the present disclosure.

At 906, ECAP waveforms 1104-1112 resulting from the plurality of SCS waveforms 1016-1024 are measured, for example, by the sensor circuitry 158. FIG. 11 is a graphical representation 1100 of the ECAP waveforms 1104-1112 measured proximate to the nerve tissue of interest (e.g., the spinal cord 308, Aβ sensory fibers). The ECAP waveforms 1104-1112 are shown aligned based on peaks 1124-1132 of each ECAP waveforms 1104-1112. A horizontal axis 1122 represents time, and a vertical axis 1120 may represent voltage or electrical potential. The sensing circuitry 158 may acquire the ECAP waveforms 1100, resulting from the plurality of SCS waveforms 1016-1024, by measuring a voltage or electrical potential of one or more of the lead electrodes 311a-h proximate to the nerve tissue of interest. The sensing circuitry 158 may utilize one or more of the lead electrodes 3111a-h to measure the ECAP waveforms 1104-1112. Each of the ECAP waveforms 1104-1112 correspond to one of the SCS waveforms 1016-1024, respectively. For example, the ECAP waveform 1104 corresponds to the SCS waveform 1016; the ECAP waveform 1106 corresponds to the SCS waveform 1018; the ECAP waveform 1108 corresponds to the SCS waveform 1020; the ECAP waveform 1110 corresponds to the SCS waveform 1022; and the ECAP waveform 1112 corresponds to the SCS waveform 1024.

Figure 12:
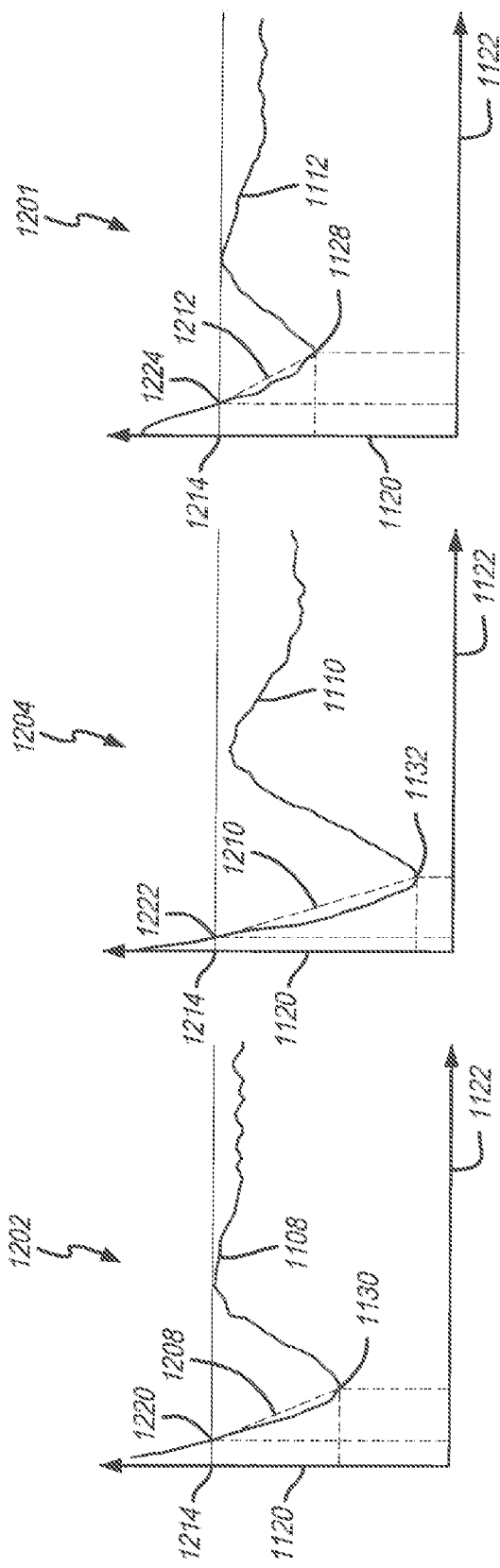
FIG. 12 are three graphical representations of evoked compound action potential waveforms, according to an embodiment of the present disclosure.

At 908, the method 900 determines slopes 1208-1212 for each ECAP waveform 1104-1112. FIG. 12 illustrates three graphical representations 1202-1206, from the graphical representation 1100 shown in FIG. 11, of the ECAP waveforms 1108-1112, respectively. The controller 151 may determine the slopes 1208-1212 for each ECAP waveform 1108-1112 based on a predetermined baseline 1214 and the peak 1124-1132 of the ECAP waveform 1104-1112. The slopes 1208-1212 may represent a ratio of the voltage change (e.g., vertical axis 1120) and the change in time (e.g., horizontal axis 1122) of the ECAP waveform 1104-1112 at the predetermined baseline 1220-1224 to the peaks 1130, 1132, and 1128, respectively. The predetermined baseline 1214 may be the common ground of the NS system 100. Optionally, the predetermined baseline 1214 may be received by the IPG 308 from the external device 160.

Figure 13:
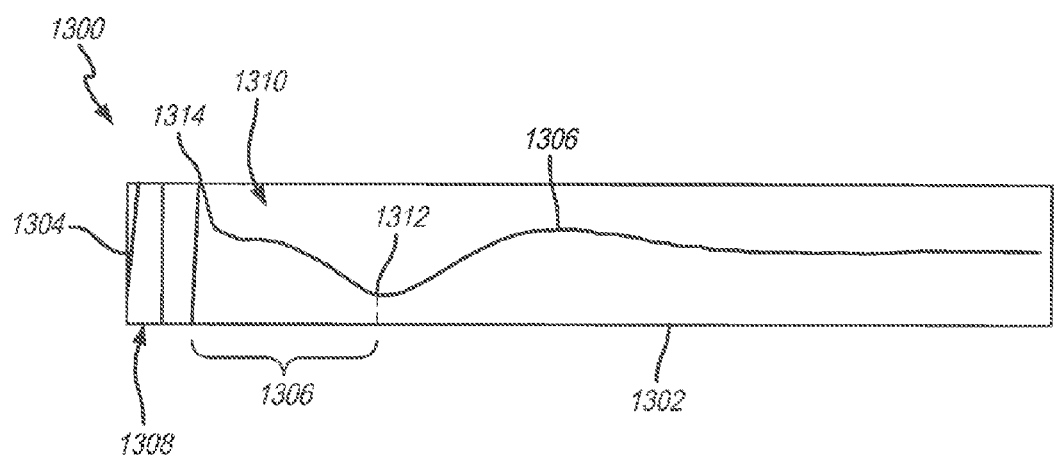
FIG. 13 is a graphical representation of a sensed electrical potential consisting of an artifact of spinal cord stimulation pulse and an evoked compound action potential generated by a nerve tissue of interest.

At 910, the method 900 determines a time delay between the onset of SCS (e.g., a stimulation spike 1314) and above one or more fiducial points 1312 for each of the ECAP waveforms 1104-1112. FIG. 13 is a graphical representation 1300 of electrical potential measurements of the nerve tissue of interest at a lead electrode (e.g., one of the lead electrodes 311a-h) for an ECAP waveform 1310 representing one of the ECAP waveforms 1104-1112. A horizontal axis 1302 represents time, and a vertical axis 1304 may represent voltage or electrical potential. An SCS waveform 1308, configured as a tonic stimulation waveform, is emitted from the lead electrode. After the SCS waveform 1308, the ECAP waveform 1310 is measured utilizing the sensing circuitry 158. The ECAP waveform 1310 includes a stimulation spike 1314 corresponding to the onset of the SCS and a minimum peak of the ECAP waveform 1310. The minimum peak may be assigned by the controller as the fiducial point 1312 for determining the time delay. It should be noted that in other embodiments more than one fiducial point may be assigned based on a maximum peak, maximum or minimum slope, a morphology point of interest of the ECAP waveform 1310, or the like. The controller 151 may calculate the time delay 1306 between the stimulation spike 1314 and the fiducial point 1312 (e.g., the minimum peak) of the ECAP waveform 1310.

Next at 912, a stimulation threshold is defined based on a stimulation amplitude and at least one of an amplitude, the slope (ascending or descending), a maximum, a minimum, or time delay between the onset of the SCS and above one or more fiducial point of the ECAP waveforms. For example, the controller 151 may compare the time delays (e.g., the time delay 1306) of each the ECAP waveforms 1104-1112, and determine an increase in the time delay beyond a predetermined threshold indicates that the stimulation threshold has been reached. The controller 151 may define the stimulation amplitude, corresponding to the SCS waveform (e.g., such as the stimulation amplitude) resulting in the increased time delay, as the stimulation threshold.

In at least one embodiment, the controller 151 may determine a decrease in the magnitude of the slope 1208-1212 corresponds to overstimulation of the neurons of the nerve tissue of interest indicating that the stimulation threshold has been reached. For example, the ECAP waveforms 1108-1112 each correspond to the SCS waveforms 1020-1024 with different predetermined stimulation amplitudes 1008-1012. The controller 151 compares the slopes 1208 and 1210, and the slopes 1210 and 1212 resulting from the SCS waveforms 1020-1024 having predetermined stimulation amplitudes 1008-1012, respectively. The controller 151 determines that the magnitude of the slope 1210 is greater than the magnitude of the slope 1208. The controller 151 determines that the magnitude of the slope 1212 is lower than the magnitude of the slope 1210, indicating overstimulation. The controller 151 defines the stimulation threshold as the predetermined stimulation amplitude 1010, which corresponds to the SCS waveform 1022 resulting in the ECAP waveform 1110 (e.g., prior to the reduced magnitude of slope 1212). Optionally, the controller 151 may determine the stimulation threshold has been reached when the magnitude of slope is reduced by a predetermined threshold.

Figure 14:
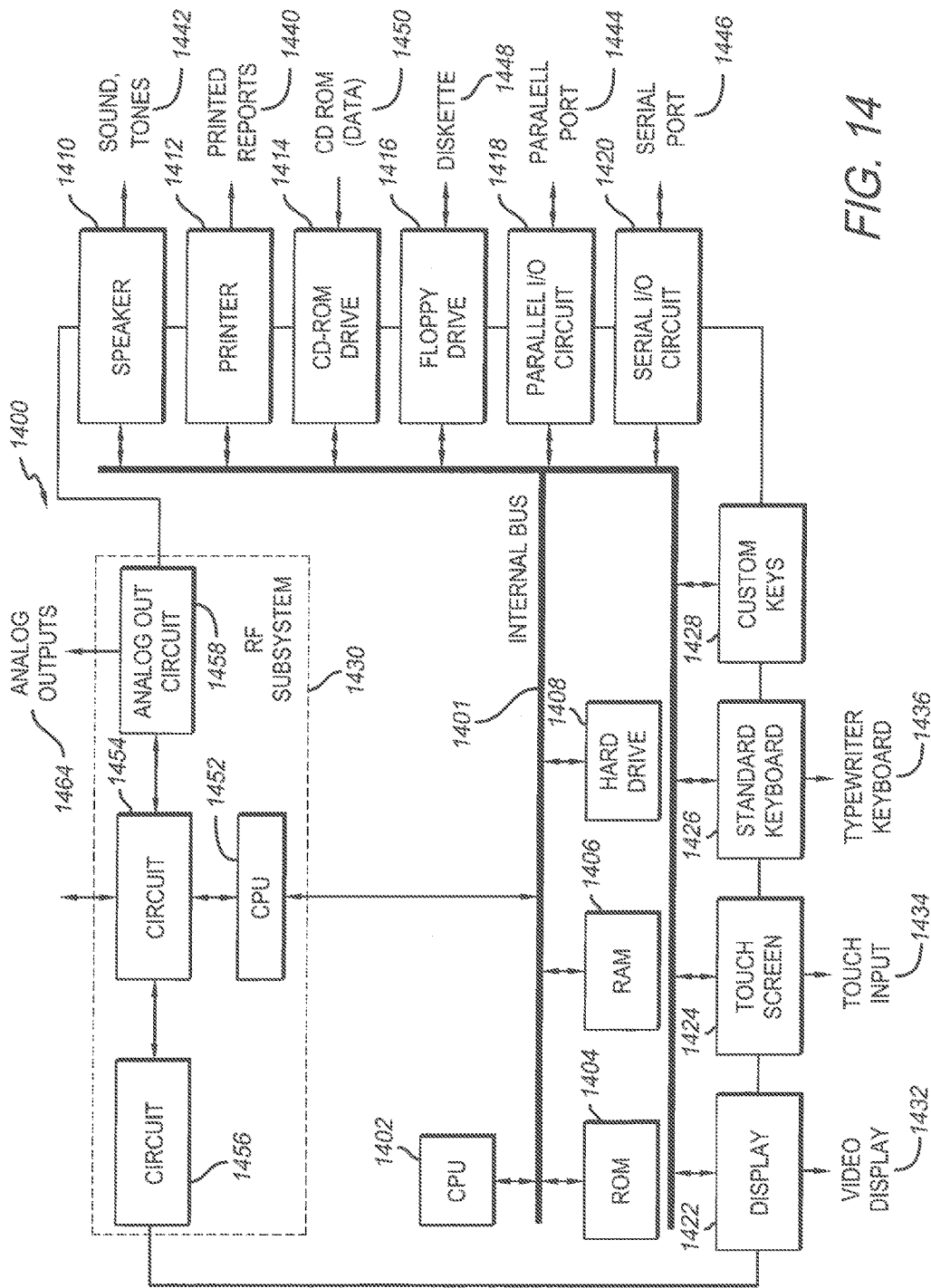
FIG. 14 illustrates a block diagram of exemplary internal components of an external device, according to an embodiment of the present disclosure.

FIG. 14 illustrates a functional block diagram of an external device 1400, according to at least one embodiment, that is operated in accordance with the processes described herein and to interface with the NS system 100 as described herein. The external device 1400 may be a workstation, a portable computer, a tablet computer, a PDA, a cell phone and the like. The external device 1400 includes an internal bus 1401 that may connect/interface with a Central Processing Unit ("CPU") 1402, ROM 1404, RAM 1406, a hard drive 1408, a speaker 1410, a printer 1412, a CD-ROM drive 1414, a floppy drive 1416, a parallel I/O circuit 1418, a serial I/O circuit 1420, the display 1422, a touchscreen 1424, a standard keyboard 1426, custom keys 1428, and an RF subsystem 1430. The internal bus 1401 is an address/data bus that transfers information between the various components described herein. The hard drive 1408 may store operational programs as well as data, such as stimulation waveform templates and detection thresholds.

The CPU 1402 typically includes a microprocessor, a microcontroller, or equivalent control circuitry, designed specifically to control interfacing with the external device 1400 and with the NS system 100. The CPU 1402 may include RAM or ROM memory, logic and timing circuitry, state machine circuitry, and I/O circuitry to interface with the NS system 100. The display 1422 (e.g., may be connected to the video display 1432). The display 1422 displays various information related to the processes described herein. The touchscreen 1424 may display graphic information relating to the NS system 100 (e.g., stimulation levels, SCS waveforms, ECAP measurements, the SCS therapy applied) and include a graphical user interface. The graphical user interface may include graphical icons, scroll bars, buttons, and the like which may receive or detect user or touch inputs 1434 for the external device 1400 when selections are made by the user. Optionally the touchscreen 1424 may be integrated with the display 1422. The keyboard 1426 (e.g., a typewriter keyboard 1436) allows the user to enter data to the displayed fields, as well as interface with the RF subsystem 1430. Furthermore, custom keys 1428, for example, may turn on/off the external device 1400. The printer 1412 prints copies of reports 1440 for a physician to review (e.g., ECAP waveforms) or to be placed in a patient file, and the speaker 1410 provides an audible warning (e.g., sounds and tones 1442) to the user. The parallel I/O circuit 1418 interfaces with a parallel port 1444. The serial I/O circuit 1420 interfaces with a serial port 1446. The floppy drive 1416 accepts diskettes 1448. Optionally, the serial I/O port may be coupled to a USB port or other interface capable of communicating with a USB device such as a memory stick. The CD-ROM drive 1414 accepts CD ROMs 1450.

The RF subsystem 1430 includes a central processing unit (CPU) 1452 in electrical communication with an RF circuit 1454, which may communicate with both memory 1456 and an analog out circuit 1458. The analog out circuit 1458 includes communication circuits to communicate with analog outputs 1464. The external device 1400 may wirelessly communicate with the NS system 100 using a telemetry system. Additionally or alternatively, the external device 1400 may wirelessly communicate with the NS system 100 utilize wireless protocols, such as Bluetooth, Bluetooth low energy, WiFi, MICS, and the like. Alternatively, a hard-wired connection may be used to connect the external device 1400 to the NS system 100.

Optionally, the external device 1400 may transmit a stimulation database request to the IPG 150. For example, the user may instruct the external device 1400 to transmit the stimulation database request from the graphical user interface on the touchscreen 1424, the keyboard 1426, or the like. The NS system 100 receives the request via the communication circuitry 155 and transmits the stimulation database stored on the memory 161 to the external device 1400.

The controllers 151, the CPU 1402, and the CPU 1452 may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the controllers 151, the CPU 1402, and the CPU 1452 may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The controllers 151, the CPU 1402, and the CPU 1452 may execute a set of instructions that are stored in one or more storage elements, in order to process data. The storage elements may also store data or other information as desired or needed. The storage element may be in the form of an information source or a physical memory element within the controllers 151, the CPU 1402, and the CPU 1452. The set of instructions may include various commands that instruct the controllers 151, the CPU 1402, and the CPU 1452 to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A method for determining a stimulation threshold for closed loop spinal cord stimulation (SCS), the method comprising:
   providing a lead coupled to an implantable pulse generator (IPG), the IPG having a processor, wherein the lead includes at least one lead electrode and is configured to be implanted at a target position proximate to nerve tissue of interest, and further wherein the processor preforming the steps of;
   delivering SCS pulses from the IPG to the lead electrodes in accordance with an SCS therapy;
   determining an evoked compound action potential (ECAP) amplitude based on an ECAP waveform resulting from the SCS therapy;
   increasing the SCS therapy by increasing at least one of an amplitude, a duration and a number of the SCS pulses associated with the SCS therapy;
   iteratively repeating the delivering, determining and increasing operations until ECAP amplitude exhibits a downward trend divergence; and
   defining a stimulation threshold based on the ECAP amplitude at the trend divergence.

2. The method of claim 1, wherein the downward trend divergence is exhibited when the ECAP amplitude during an Nth iteration of the delivering, determining and increasing operations is lower than an average ECAP amplitude during a plurality of previous iterations of the delivering, determining and increasing operations.

3. The method of claim 1, wherein the stimulation threshold corresponds to at least one of the amplitude, the duration, the number of SCS pulses associated with the SCS therapy.

4. The method of claim 1, further comprising, during the iteratively repeating steps and subsequent to each step of determining an ECAP amplitude, calculating an average ECAP amplitude based upon the determined ECAP amplitudes;
   and further, subsequent to the step of defining a stimulation threshold, changing the SCS therapy by delivering SCS pulses from the IPG with the amplitude of the SCS pulses at or below the defined stimulation threshold;
   determining the ECAP amplitude based on an ECAP waveform resulting from the changed SCS therapy;
   comparing the determined ECAP amplitude resulting from the changed SCS therapy with the calculated average ECAP amplitude; and
   reducing the stimulation level if it is determined that the ECAP amplitude resulting from the changed SCS therapy is lower than the calculated average ECAP amplitude.

5. The method of claim 1, further comprising defining a suprathreshold zone and a subthreshold zone based on the stimulation threshold.

6. The method of claim 1, further comprising recording an ECAP waveform based on the ECAP measurements onto a stimulation database; and once a transmission request is received from an external device, wirelessly transmitting the stimulation database to the external device.

7. The method of claim 1, further comprising measuring the ECAP waveform proximate to an Aβ sensory fiber.

8. The method of claim 1, further comprising determining a stimulation baseline.

9. The method of claim 1, further comprising transmitting an alert notification once the stimulation threshold is defined.

10. A system for determining a stimulation threshold for closed loop spinal cord stimulation comprising:
    a lead having at least one lead electrode, the lead configured to be implanted at a target position proximate to or within nerve tissue of interest;
    an implantable pulse generator (IPG) coupled to the lead, the IPG configured to deliver SCS pulses to the lead electrodes in accordance with an SCS therapy;

the IPG including a sensing circuitry configured to measure an evoked compound action potential (ECAP) waveform resulting from the SCS therapy;

the IPG further including a processor in communication with the sensing circuitry, the processor programmed to operation, in response to instructions stored on a non-transient computer-readable medium to:

determine an ECAP amplitude based on the ECAP waveform;

increase the SCS therapy by increasing at least one of an amplitude, a duration and a number of the SCS pulses associated with the SCS therapy;

iteratively repeat the determine and increase operations until an increasing trend or a plateau in the ECAP amplitude exhibits a downward trend divergence; and define a stimulation threshold based on the ECAP amplitude at the trend divergence.

11. The system of claim 10, wherein the downward trend divergence is exhibited when the ECAP amplitude delivered during an Nth iteration of the determine and increase operations of the processor is lower that an average ECAP amplitude, during a plurality of previous iterations of the determine and increase operations of the processor.

12. The system of claim 10, wherein the processor is configured to define a suprathreshold zone and a subthreshold zone based on the stimulation threshold.

13. The system of claim 10, wherein the ECAP is measured proximate to the $A\beta$ sensory fiber.

14. The method of claim 10, wherein the IPG further includes RF circuitry in communication with the processor, the processor is configured to output an alert notification to the RF circuitry once the stimulation threshold is defined.

* * * * *